United States Patent [19]

Oliver et al.

[11] Patent Number: 5,075,443

[45] Date of Patent: Dec. 24, 1991

[54] PREPARATION OF 2-AMINO-4-ALKOXY-S-TRIAZINES

[75] Inventors: Michael A. Oliver; Ward H. Oliver, both of Baton Rouge, La.

[73] Assignee: Ciba-Geigy Corporation, Ardsley, N.Y.

[21] Appl. No.: 562,161

[22] Filed: Aug. 3, 1990

[51] Int. Cl.$^5$ .......................................... C07D 251/16
[52] U.S. Cl. ..................................... 544/194; 544/211
[58] Field of Search ................................ 544/194, 211

[56] References Cited

U.S. PATENT DOCUMENTS 3,154,547 10/1964 Huffmann ..................... 260/249.5
4,298,544 11/1981 Robinson ..................... 260/453
4,587,337 5/1986 Weiss .......................... 544/194
4,886,881 12/1989 Chiang ........................ 544/194

*Primary Examiner*—John M. Ford
*Attorney, Agent, or Firm*—Kevin T. Mansfield; Edward McC. Roberts

[57] ABSTRACT

2-Amino-4-alkoxy-s-triazines which are substituted by an alkyl, aryl or aralkyl moiety in the 6-position and which are useful as pharmaceutical agents and as intermediates for herbicides, dyes and optical brighteners are prepared by reacting a dialkyl (N-cyanoimido)carbonate with an amidine salt in the presence of an inert solvent and a base.

16 Claims, No Drawings

PREPARATION OF 2-AMINO-4-ALKOXY-S-TRIAZINES

This invention relates to a process for the preparation of 2-amino-4-alkoxy-s-triazines. More particularly it relates to a process for the preparation of 2-amino-4-alkoxy-s-triazines which are substituted by an alkyl, aryl or aralkyl moiety in the 6-position which comprises reacting a dialkyl (N-cyanoimido)carbonate with an amidine salt in the presence of a solvent and a strong base.

2-Amino-4-alkoxy-s-triazines are important products which find use as pharmaceutical agents and as intermediates for herbicides, dyes and optical brighteners. Many routes to said compounds are known and are discussed for example in U.S. Pat. Nos. 3,154,547, 4,587,337 and 4,886,881. In general the processes of the prior art are not satisfactory for use on an industrial scale from the standpoint of low overall yields from readily available starting materials, extended cycle time, cost, safety and/or environmental problems.

It has now been found that 2-amino-4-alkoxy-s-triazines which are substituted by an alkyl, aryl or aralkyl group in the 6-position can be prepared in good yield and quality from readily available starting materials by a process which comprises reacting a dialkyl (N-cyanoimido)carbonate with an amidine salt in the presence of an inert solvent and a base. Preferred 2-amino-4-alkoxy-s-triazines are of the formula I

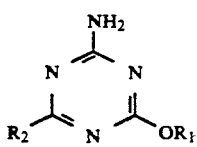

wherein
$R_1$ is $C_1$–$C_4$alkyl or $C_1$–$C_2$alkoxy-$C_1$–$C_2$alkyl and
$R_2$ is $C_1$–$C_8$alkyl which is unsubstituted or substituted by $C_1$–$C_4$alkoxy, phenyl or phenyl substituted by $C_1$–$C_4$alkyl, $C_1$–$C_4$alkoxy, difluoromethyl, trifluoromethyl, halo or nitro; phenyl or phenyl substituted by $C_1$–$C_4$alkyl, $C_1$–$C_4$alkoxy, difluoromethyl, trifluoromethyl, halo or nitro; $C_3$–$C_6$cycloalkyl or allyl.

The alkyl groups occurring in the substituents $R_1$ and $R_2$ may be straight-chain or branched. $R_1$ is for example, methyl, ethyl, n-propyl, isopropyl, n-butyl, sec-butyl and tert-butyl, with methyl and ethyl preferred. $R_2$ as $C_1$–$C_8$ alkyl includes all of the above plus the isomeric pentyl, hexyl, heptyl and octyl radicals, with the $C_1$–$C_4$ alkyl groups, particularly methyl, ethyl and isopropyl, preferred.

$C_1$–$C_4$ Alkoxy includes methoxy, ethoxy, n-propoxy, isopropoxy and the four isomeric butoxy radicals, but in particular methoxy and ethoxy.

The optionally substituted phenyl and alkylphenyl groups as $R_2$ are, for example, phenyl, 2-chlorophenyl, 3-chlorophenyl, 4-chlorophenyl, 2,4-dichlorophenyl, 4-fluorophenyl, 4-methoxyphenyl, 2,4-dimethoxyphenyl, 4-trifluoromethylphenyl, benzyl, 4-methylbenzyl, 4-nitrobenzyl, 4-bromobenzyl or 2-phenylethyl. Phenyl is preferred.

Halo substituents are fluoro, chloro, or bromo.

$C_3$–$C_6$-Cycloalkyl includes cyclopropyl, cyclobutyl, cyclopentyl and cyclohexyl with cyclopropyl preferred.

Particularly preferred compounds of formula I are those wherein $R_1$ is methyl and $R_2$ is methyl, ethyl or cyclopropyl.

The preferred dialkyl (N-cyanoimido)carbonates are of the formula II

wherein $R_1$ is as defined for formula I.

The preferred amidine salts are of the formula III

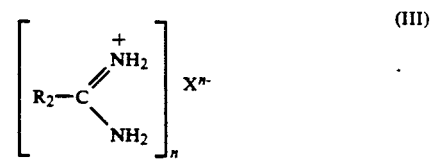

wherein $R_2$ is as defined for formula I, X is the anion of an inorganic or organic acid and n is the number 1 or 2. Preferred meanings of X are halide, especially chloride, sulfate, bisulfate and acetate.

The dialkyl (N-cyanoimido)carbonates of formula II and amidine salts of formula III are known compounds or can be prepared by known methods. See for example *The Chemistry of Amidines and Imidates,* Saul Patai Ed., John Wiley & Sons, (1975).

The reaction of a dialkyl (N-cyanoimido)carbonate with an amidine salt to form a 2-amino-alkoxy-s-triazine is carried out in the presence of a solvent and a strong base.

Suitable solvents are alcohols of the formula $R_1OH$ wherein $R_1$ preferably corresponds to the $R_1$ alkyl groups of the dialkyl (N-cyanoimido)carbonate, open chain or cyclic ethers such as methyl tert-butyl ether or tetrahydrofuran, $C_3$–$C_7$ketones such as acetone and methyl isobutyl ketone, $C_5$–$C_{12}$hydrocarbons such as hexane, $C_1$–$C_6$hydrocarbons substituted by 1–6 halogens such as methylene chloride, benzene or benzene substituted by 1 or 2 halogens or $C_1$–$C_3$alkyl groups such as toluene, or a mixture thereof. Preferred mixtures contain an alcohol $R_1OH$ with at least one of the other solvents. Water can also be used as one of the solvents when the amidine is hydrolytically stable. The amount of solvent is not critical as long as the amount is sufficient to maintain good stirability.

Suitable strong bases include the alkali metal alkoxides of the alcohols $R_1OH$. Alkali metal hydroxides and alkali earth metal hydroxides may also be employed if the amidine is hydrolytically stable. About stoichiometric amounts of base are preferred.

Reaction temperatures can range from about −20° to 50° C., preferably from about −10° to 25° C.

The reactants can be combined in any order. The preferred method of carrying out the reaction is to add the base to a mixture of the amidine salt and the dialkyl (N-cyanoimido)carbonate with stirring and cooling. The addition rate is not critical but should be slow enough to maintain the temperature in the range indicated above. In the lab, good results have been obtained with addition times of 10 minutes to 2 hours. The reaction is essentially complete when the addition of the base is finished.

The invention may be illustrated by the following nonlimiting examples.

EXAMPLE 1

2-Amino-4-isopropyl-6-methoxy-s-triazine

A. To a 100 ml. flask charge 20 ml. dry methanol. With ice bath cooling, saturate with anhydrous HCl (about 10 gm.). With stirring and ice bath cooling, add dropwise 6.9 gm. (0.2 mole) isobutyronitrile while maintaining the temperature below 10° C. Allow the solution to rise to room temperature and stir the methyl isobutyrimidate thus prepared an additional hour.

B. To a 250 ml. flask, charge 7.5 gm. (0.13 mole) 30% aqueous ammonia, and 10 ml. water. With ice bath cooling, charge the methyl isobutyrimidate solution dropwise, maintaining the temperature below 10° C. and the pH at 9.5-9.8 with 25% NaOH. When all the imidate has been added, adjust the pH to 9.0-9.5 and allow to stir at room temperature one hour to give isobutyramidine hydrochloride.

C. Cool the isobutyramidine hydrochloride solution in an ice bath. Charge 8 gm. (0.07 mole) dimethyl (N-cyanoimido)carbonate to the solution, followed by 5.8 gm. (0.073 mole) 50% NaOH, added dropwise. Stir while letting the mixture warm to room temperature for one hour. Remove the methanol by vacuum stripping, and slurry the resulting solids in 75 ml. water. Cool and filter. Upon drying, 7.2 gm. (61.2%) 2-amino-4-isopropyl-6-methoxy-s-triazine is obtained, mp 116°-117° C.

EXAMPLE 2

2-Amino-4-methoxy-6-methyl-s-triazine

To a 100 ml. flask charge 5.5 gm. acetamidine hydrochloride, 5.7 gm. dimethyl (N-cyanoimido)carbonate, 11 gm. methanol and 11 gm. toluene. Cool the mixture to 5° C. and add dropwise 11.8 gm. of 30% sodium methoxide while maintaining the reaction temperature at 5°-10° C. When the addition is complete, warm the reaction mixture to room temperature. Filter the slurry and wash the filter cake with methanol. Reslurry the filtercake in water, filter, wash the filter cake with water. Dry the solids to give 6.1 gm. (87%) 2-amino-4-methoxy-6-methyl-s-triazine, mp 256°-258° C.

EXAMPLE 3

2-Amino-4-ethoxy-6-methyl-s-triazine

To a 250 ml. round-bottomed flask charge 5 gm. (0.05 mole) 95% acetamidine hydrochloride, 10 gm. (0.088 mole) diethyl (N-cyanoimido)carbonate, and 50 gm. ethanol. Cool the stirred solution to 0° C., and add 30 ml. ethanol solution containing 4 gm. (0.056 mole) sodium ethoxide over 30 minutes. Allow the temperature of the reaction mass to rise to room temperature and stir one hour. Filter the resulting slurry. Vacuum strip the ethanol from the filtrate until solids appear. Add the solids from the filter to this residue and add 50 ml. water. Stir the slurry and filter. Dry the solids to obtain 6.6 gm. (85.7%) 2-amino-4-ethoxy-6-methyl-s-triazine, mp 172°-174° C.

EXAMPLE 4

2-Amino-4-cyclopropyl-6-ethoxy-s-triazine

To a 250 ml. flask charge 30 gm. of an aqueous solution containing 0.05 moles cyclopropane carboxamidine hydrochloride, 55 ml. methyl tert-butyl ether, and 9 gm. diethyl (N-cyanoimido) carbonate at 5° C. Charge dropwise 7 gm. 30% NaOH solution. Allow the temperature of the mixture to rise to room temperature and stir one hour. Add water to dissolve the salt, and separate the layers. Extract the water layer two times with 20 ml. methyl tert-butyl ether, combine the extracts and strip the solvent to yield 6.8 gm. (75.5%) 2-amino-4-cyclopropyl6-ethoxy-s-triazine, mp 103°-106° C.

EXAMPLE 5

2-Amino-4-cyclopropyl-6-methoxy-s-triazine

To a 250 ml. flask charge 30 gm. of an aqueous solution containing 0.05 mole cyclopropane carboxamidine hydrochloride, 20 ml. methylene chloride, and 6.2 gm (0.054 mole) dimethyl (N-cyanoimido)carbonate dissolved in 70 ml. methylene chloride. Control the temperature at 5° C. and slowly charge 7 gm. (0.053 mole) 30% NaOH solution. Remove cooling and stir for one hour at room temperature. Filter the slurry and dry the solids to yield 6.3 gm. (75.9%) 2-amino-4-cyclopropyl-6-methoxy-s-triazine, mp 162°-165° C.

EXAMPLE 6

2-Amino-4-methoxy-6-phenyl-s-triazine

To a 250 ml. flask charge 9.2 gm. (0.05 mole) 85% benzamidine hydrochloride, 75 ml. methanol, and 6 gm. (0.053 mole) dimethyl (N-cyanoimido)carbonate. At 5° C., charge dropwise 7 gm. (0.053 mole) 30% NaOH solution. Stir at room temperature one hour. Strip the methanol solvent, and slurry the solids in 75ml. water. Filter and dry the product to yield 9.2 gm. (91%) 2-amino-4-methoxy-6-phenyl-s-triazine, mp 159°-160.5° C.

What is claimed is:

1. A process for the preparation of a 2-amino-4-alkoxy-s-triazine of the formula I

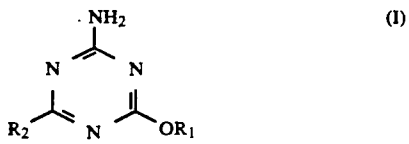

wherein $R_1$ is $C_1$-$C_4$alkyl or $C_1$-$C_2$alkoxy-$C_1$-$C_2$alkyl and $R_2$ is $C_1$-$C_4$alkyl which is unsubstituted or substituted by $C_1$-$C_4$alkoxy, phenyl or phenyl substituted by $C_1$-$C_4$alkyl, $C_1$-$C_4$alkoxy, difluoromethyl, trifluoromethyl, halo or nitro, phenyl or phenyl substituted by $C_1$-$C_4$alkyl, $C_1$-$C_4$alkoxy, difluoromethyl, trifluoromethyl, halo or nitro; $C_3$-$C_6$cycloalkyl or allyl, which comprises reacting an (N-cyanoimido)carbonate of the formula II

wherein $R_1$ is as defined for formula I with an amidine salt of the formula III

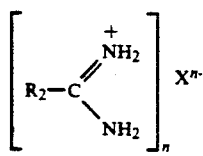

(III)

wherein $R_2$ is as defined for formula I, X is the anion of an inorganic or organic acid and n is the number 1 or 2, in the presence of a solvent and a strong base.

2. A process according to claim 1, wherein $R_1$ is methyl or ethyl and $R_2$ is $C_1$-$C_4$alkyl, cyclopropyl or phenyl.

3. A process according to claim 2, wherein $R_1$ is methyl and $R_2$ is methyl, ethyl or cyclopropyl.

4. A process according to claim 3, wherein $R_1$ and $R_2$ are each methyl.

5. A process according to claim 1, wherein n is the number 1 and X is a halide, bisulfate or acetate anion, or wherein n is the number 2 and X is the sulfate anion.

6. A process according to claim 5, wherein n is the number 1 and X is the chlorine anion.

7. A process according to claim 1, wherein the solvent is water, an alcohol of the formula $R_1OH$ wherein $R_1$ is defined for formula I, an open chain or cyclic ether, a $C_3$-$C_7$ketone, a $C_5$-$C_{12}$hydrocarbon, a $C_1$-$C_6$-hydrogen substituted by 1-6 halogens, benzene or a phenyl substituted by 1 or 2 halogens or $C_1$-$C_3$alkyl groups, or a mixture thereof.

8. A process according to claim 7, wherein the solvent is water, methanol, ethanol, methyl tert-butyl ether, toluene or methylene chloride, or a mixture thereof.

9. A process according to claim 8, wherein the solvent is a mixture of methanol and toluene.

10. A process for the preparation of a 2-amino-4-alkoxy-s-triazine which is substituted by an alkyl, aryl or aralkyl group in the 6-position which comprises reacting a dialkyl (N-cyanoimido)carbonate with an amidine salt in the presence of a solvent and a strong base.

11. A process according to claim 10, wherein the strong base is an alkali metal salt of a $C_1$-$C_4$alcohol.

12. A process according to claim 10, wherein the strong base is an alkali metal hydroxide or alkali earth metal hydroxide.

13. A process according to claim 12, wherein the strong base is solid sodium hydroxide or sodium hydroxide dissolved in water.

14. A process according to claim 10, wherein the temperature is in the range of $-20°$ to $50°$ C.

15. A process according to claim 10, wherein the temperature is in the range of $-10°$ to $25°$ C.

16. A process according to claim 10, which comprises adding a methanolic solution of sodium methoxide to a stirred mixture of dimethyl (N-cyanoimido)carbonate and acetamidine hydrochloride, in methanol and toluene as solvent, at a temperature in the range of $5°$-$10°$ C., and stirring until the reaction is essentially complete.

* * * * *